United States Patent [19]

Ryono et al.

[11] Patent Number: 4,665,193
[45] Date of Patent: May 12, 1987

[54] AMINO ACID ESTER RENIN INHIBITORS

[75] Inventors: Denis E. Ryono, Princeton; Edward W. Petrillo, Jr., Pennington, both of N.J.

[73] Assignee: E. R. Squibb & Sons, Inc., Princeton, N.J.

[21] Appl. No.: 879,693

[22] Filed: Jun. 27, 1986

Related U.S. Application Data

[60] Division of Ser. No. 681,756, Dec. 14, 1984, Pat. No. 4,616,088, which is a continuation-in-part of Ser. No. 666,015, Oct. 29, 1984, abandoned.

[51] Int. Cl.$^4$ ........................................... C07D 233/64
[52] U.S. Cl. .................................... 548/344; 546/256; 546/261; 546/265; 546/273; 546/278; 546/283; 546/284; 546/291; 546/316; 546/323; 546/335; 548/336; 548/484; 548/486; 548/492; 548/495; 548/496; 549/60; 549/65; 549/72; 549/76; 549/77; 549/473; 560/31; 549/479; 560/32; 560/115; 549/487; 560/121; 560/122; 549/493; 560/123; 560/125; 560/13; 560/148; 560/153; 560/16; 560/159; 560/169; 560/24; 560/27; 560/29; 560/30

[58] Field of Search ............... 548/344, 336, 484, 486, 548/492, 495, 496; 546/256, 261, 265, 273, 278, 283, 284, 291, 316, 323, 335; 549/60, 65, 72, 76, 77, 473, 479, 487, 493; 560/13, 16, 24, 27, 29, 30, 31, 32, 115, 121, 122, 123, 125, 148, 153, 159, 169

[56] References Cited

U.S. PATENT DOCUMENTS 4,470,973 9/1984 Natarajan et al. ............... 546/245 X
4,514,391 4/1985 Gordon et al. ........................ 514/2

FOREIGN PATENT DOCUMENTS 104041 3/1984 European Pat. Off. ............ 548/344

Primary Examiner—Richard A. Schwartz
Attorney, Agent, or Firm—Lawrence S. Levinson; Stephen B. Davis

[57] ABSTRACT

Compounds of the formula

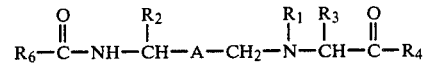

wherein A is

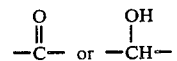

intervene in the conversion of angiotensinogen to angiotensin II by inhibiting renin and thus are useful as anti-hypertensive agents.

5 Claims, No Drawings

AMINO ACID ESTER RENIN INHIBITORS

PRIOR APPLICATIONS

This application is a division of Ser. No. 681,756 filed on Dec. 14, 1984, now U.S. Pat. No. 4,616,088, which was a continuation-in-part of U.S. Ser. No. 665,015 filed Oct. 29, 1984, now abandoned.

BACKGROUND OF THE INVENTION

Szelke et al. in European Patent Application 104,041 disclose renin inhibitory polypeptides including the partial sequence

X-A-B-Z-W wherein A is

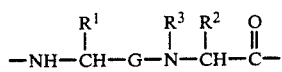

and G is

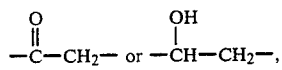

X is hydrogen, protecting group or an amino acyl residue, B is a lipophilic amino acyl residue, and Z plus W are an amino alcohol residue or Z is aminoacyl and W is hydroxy, ester, amide, etc.

Natarajan et al. in U.S. Pat. No. 4,470,973 disclose aminoketone carboxylic acids of the formula

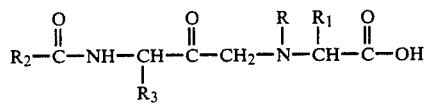

as intermediates in the preparation of aminoketone peptides which possess angiotensin converting enzyme or enkephalinase inhibition activity.

Gordon et al. in U.S. application Ser. No. 515,729 filed July 21, 1983, now U.S. Pat. No. 4,514,381 disclose hydroxy substituted peptide compounds of the formula

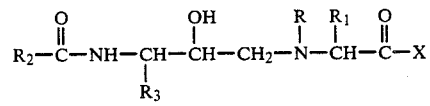

which possess angiotensin converting enzyme or enkephalinase inhibition activity.

SUMMARY OF THE INVENTION

This invention is directed to new amino acid ester and amide compounds of formula I including pharmaceutically acceptable salts thereof

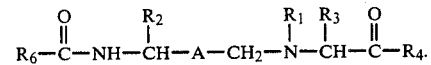

A is

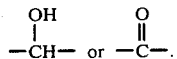

$R_4$ is —O—lower alkyl, —O—$(CH_2)_m$-aryl, —O—$(CH_2)_m$-heterocyclo, or

$R_5$ is hydrogen, lower alkyl, —$(CH_2)_m$-aryl, or —$(CH_2)_m$-heterocyclo.

m is zero, one, two, three or four.

$R_6$ is lower alkyl, —$(CH_2)_m$-aryl, —$(CH_2)_m$-heterocyclo, or

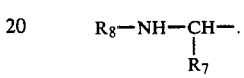

$R_8$ is hydrogen,

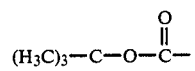

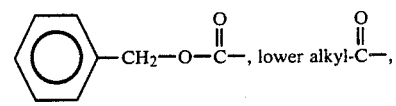

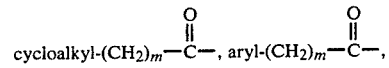

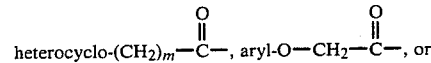

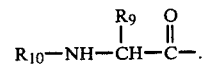

$R_{10}$ is hydrogen,

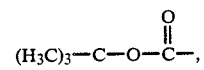

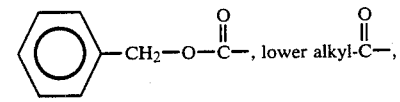

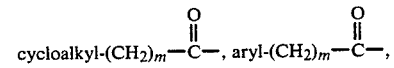

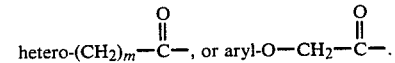

$R_2$, $R_3$, $R_7$ and $R_9$ are independently selected from the group consisting of hydrogen, lower alkyl, halo substituted lower alkyl, —$(CH_2)_n$-aryl, —$(CH_2)_n$-heterocyclo, —$(CH_2)_n$—OH, —$(CH_2)_n$—$NH_2$, —$(CH_2)_n$—SH, —$(CH_2)_n$—S-lower alkyl, —$(CH_2)_2$—S—$(CH_2)_2$—$NH_2$,

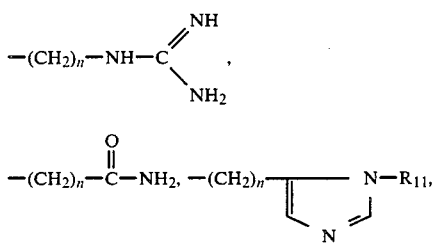

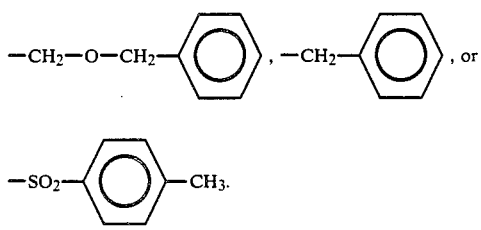

and —(CH$_2$)$_n$-cycloalkyl.

n is an integer from 1 to 4.

R$_{11}$ is

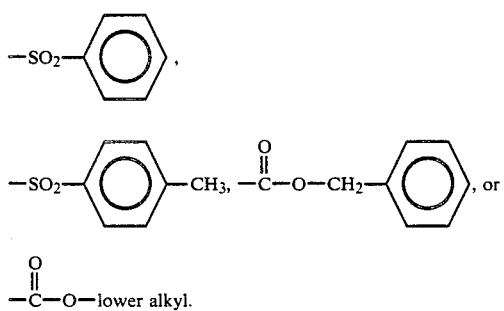

R$_1$ is hydrogen, lower alkyl, —(CH$_2$)$_n$-aryl, —(CH$_2$)$_n$-cycloalkyl,

—SO$_2$—⟨phenyl⟩,

—SO$_2$—⟨phenyl⟩—CH$_3$, —C(=O)—O—CH$_2$—⟨phenyl⟩, or

—C(=O)—O—lower alkyl.

DETAILED DESCRIPTION OF THE INVENTION

This invention in its broadest aspects relates to the amino acid ester and amide compounds of formula I above, to compositions and the method of using such compounds as antihypertensive agents.

The term lower alkyl used in defining various symbols refers to straight or branched chain radicals having up to seven carbons, preferably from one to four carbons. Similarly, the terms lower alkoxy and lower alkylthio refer to such lower alkyl groups attached to an oxygen or sulfur.

The term cycloalkyl refers to saturated rings of 4 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)$_2$ wherein alkyl is of 1 to 4 carbons, di or tri substituted phenyl, 1-naphthyl or 2-naphthyl wherein said substituents are methyl, methoxy, methylthio, halogen, or hydroxy.

The term heterocyclo refers to fully saturated or unsaturated rings of 5 or 6 atoms containing one or two O and S atoms and/or one to four N atoms provided that the total number of hetero atoms in the ring is 4 or less. The heterocyclo ring is attached by way of an available carbon atom. Preferred heterocyclo groups include 2- and 3-thienyl, 2- and 3-furyl, 2-, 3- and 4-pyridyl, and imidazolyl. The term heterocyclo also includes bicyclic rings wherein the five or six membered ring containing O, S and N atoms are defined above is fused to a benzene ring. The preferred bicyclic ring is indolyl.

Compounds of formula I wherein A is $$-\overset{\overset{O}{\|}}{C}-$$

can be prepared as follows. A halomethyl ketone of the formula $$R_{40}-NH-\overset{R_2}{\underset{|}{C}H}-\overset{O}{\underset{\|}{C}}-CH_2-halo \qquad (II)$$

wherein R$_{40}$ is a protecting group such as $$(H_3C)_3-C-O-\overset{O}{\underset{\|}{C}}-,$$

especially wherein halo is Cl, is reacted with an amine of the formula $$\overset{R_1}{\underset{|}{H-N}}-\overset{R_3}{\underset{|}{C}H}-\overset{O}{\underset{\|}{C}}-R_4. \qquad (III)$$

This reaction is performed in the presence of sodium bicarbonate and dimethylformamide and gives the compound of the formula $$R_{40}-NH-\overset{R_2}{\underset{|}{C}H}-\overset{O}{\underset{\|}{C}}-CH_2-\overset{R_1}{\underset{|}{N}}-\overset{R_3}{\underset{|}{C}H}-\overset{O}{\underset{\|}{C}}-R_4. \qquad (IV)$$

The intermediate of formula IV is then treated to remove the R$_{40}$ protecting group such as by treatment with hydrochloric acid in the presence of ethyl acetate and the resulting amine hydrochloride salt is reacted with the carboxylic acid of the formula $$R_6-COOH \qquad (V)$$

in the presence of dicyclohexylcarbodiimide and hydroxybenzotriazole to give the desired final product.

The compounds of formula I wherein A is $$\overset{OH}{\underset{|}{-CH-}}$$

can be prepared as follows. The intermediates of formula IV is treated with a conventional reducing agent such as sodium borohydride, sodium cyanoborohydride, diisobutyl aluminum hydride, lithium tri t-butoxy aluminum hydride, etc., to give

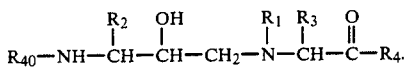 (VI)

The intermediate of formula VI is then treated to remove the $R_{40}$ protecting group and the resulting amine is reacted with the carboxylic acid of formula V as described above to give the desired final products.

The compounds of formula I wherein A is

can also be prepared by reacting an oxazolidine, trimethylsilylethyl ester of the formula

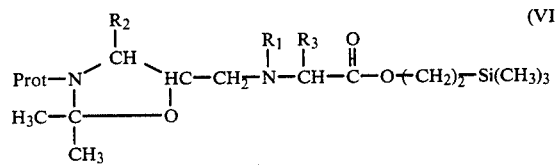 (VII)

so as to introduce the desired $R_4$ substituent. For example, when $R_4$ is $NH_2$ the ester of formula VII is treated with tetra-n-butyl ammonium fluoride, followed by isobutylchloroformate, and finally methanolic ammonia, and when $R_4$ is $-NH-R_5$ the ester of formula VII is treated with tetra n-butyl ammonium fluoride, followed by isobutylchloroformate, and finally the amine $H_2N-R_5$. The resulting oxazolidine is then treated with trifluoroacetic acid and aqueous hydrochloric acid to give the intermediate of the formula

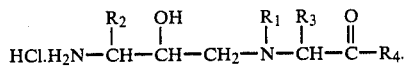 (VIII)

The intermediate of formula VIII is then treated with the carboxylic acid of formula V in the presence of dicyclohexylcarbodiimide and hydroxybenzotriazole as described above to give the desired final products.

In the above reactions, if $R_1$ is hydrogen then that N-atom would be protected for example by reacting the intermediate of formula IV with benzyloxycarbonyl chloride in the presence of pyridine and benzene. The benzyloxycarbonyl group could then be removed as the last step of the synthesis by hydrogenation in the presence of palladium on carbon catalyst.

Similarly, if any of $R_1$, $R_2$, $R_3$, $R_7$ and $R_9$ in the above reactions are $-(CH_2)_n$-aryl wherein aryl is phenyl, 1-naphthyl, 2-naphthyl substituted with one or more hydroxy or amino groups, $-(CH_2)_n$-heterocyclo wherein heterocyclo is an imidazolyl, $-(CH_2)_n-NH_2$, $-(CH_2)_n-SH$, $-(CH_2)_n-OH$, or

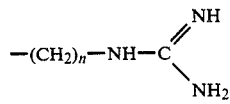

then the hydroxyl, amino, imidazolyl, mercaptan, or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or by other known means following completion of the reaction.

The starting materials of formula II can be prepared by reacting an N-protected amino acid of the formula

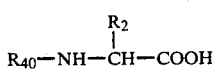 (IX)

with isobutylchloroformate, followed by diazomethane, and finally hydrochloric acid.

The oxazolidine, trimethylsilyl ethyl ester of formula VII can be prepared by reacting the halomethyl ketone of formula II with the amino acid, trimethylsilyl ester of formula

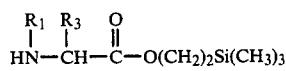 (X)

in the presence of sodium iodide, sodium bicarbonate and dimethylformamide to give the compound of the formula

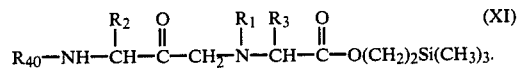 (XI)

The ketone of formula XI is reduced to the corresponding alcohol by treatment with sodium borohydride or other reducing agents as described above. This alcohol is then treated with 2-methoxypropene in the presence of a catalytic amount of pyridinium-p-toluenesulfonic acid to give the desired oxazolidine, trimethylsilyl ethyl ester.

The various peptide intermediates employed in above procedures are known in the literature or can be readily prepared by known methods. See for example, The Peptides, Volume 1, "Major Methods Of Peptide Bond Formation", Academic Press (1979).

Preferred compounds of this invention are those of formula I wherein:

A is

$R_1$ is hydrogen,

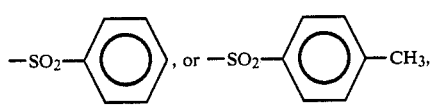

especially hydrogen.

$R_2$ is straight or branched chain lower alkyl of 1 to 4 carbons, benzyl, phenethyl, or

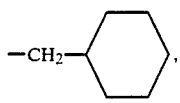

especially —CH$_2$—CH(CH$_3$)$_2$.

R$_3$ is hydrogen, straight or branched chain lower alkyl of 1 to 4 carbons, benzyl or phenethyl, especially —CH$_2$—CH(CH$_3$)$_2$ or —CH(CH$_3$)$_2$.

R$_4$ is —NH$_2$, —NH—(CH$_2$)$_n$-aryl, or —NH—(CH$_2$)$_n$-heterocyclo wherein n is one, two, or three, aryl is phenyl, and heterocyclo is pyridyl.

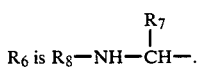

R$_7$ is

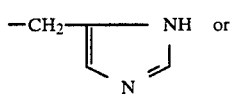

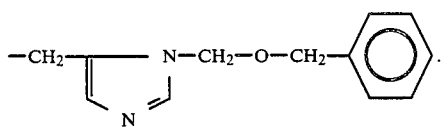

R$_8$ is

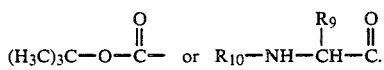

R$_9$ is —(CH$_2$)$_n$-aryl wherein aryl is phenyl or 1-naphthyl and n is one or two, especially

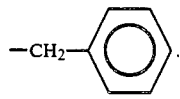

R$_{10}$ is

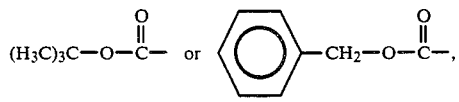

especially

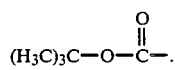

The compounds of formula I form salts with a variety of inorganic and organic acids. The non-toxic pharmaceutically acceptable salts are preferred, although other salts are also useful in isolating or purifying the product. Such pharmaceutically acceptabile salts include those formed with hydrochloric acid, methanesulfonic acid, sulfuric acid, acetic acid, maleic acid, etc. The salts are obtained by reacting the product with an equivalent amount of the acid in a medium in which the salt precipitates.

The compounds of formula I contain asymmetric centers when any or all of R$_2$, R$_3$, R$_7$, and R$_9$ are other than hydrogen. An additional asymmetric center is present when A is

Thus, the compounds of formula I can exist in diasteroisomeric forms or in mixtures thereof. The above described processes can utilize racemates, enantiomers or diastereomers as starting materials. When diastereomeric products are prepared, they can be separated by conventional chromatographic or fractional crystallization methods.

The compounds of formula I, and the pharmaceutically acceptable salts thereof, are antihypertensive agents. They inhibit the conversion of angiotensinogen to angiotensin I and therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→(ACE)→angiotensin II sequence by inhibiting renin and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 100 to 1000 mg., preferably about 250 to 500 mg. per kg. of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension.

A combination product comprising a compound of this invention and a diuretic can be administered in an effective amount which comprises a total daily dosage of about 1000 to 6000 mg., preferably about 3000 to 4000 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions or suspensions for parenteral administration. About 100 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade.

EXAMPLE 1

$N^2$-[3-[[N-[N-[(1,1-Dimethylethoxy)carbonyl]-L-phenylalanyl]-L-histidyl]amino]-2-hydroxy-5-methylhexyl]-N-[2-(2-pyridinyl)ethyl]-L-leucinamide, acetic acid salt (1:2)

(a) 3-[(Phenylmethoxy)methyl]-L-histidine, methyl ester, dihydrochloride

N-[(1,1-Dimethylethoxy)carbonyl]-3-[(phenylmethoxy)methyl]-L-histidine, methyl ester, monohydrochloride (7.8 g., 18.3 mmole) [prepared according to the procedure of Brown et al., J. Chem. Soc. Perkins Trans., Vol. 1, p. 2261 (1979)] is suspended in ethyl acetate (140 ml.) under a flow of nitrogen, cooled in an ice-water bath. Dry hydrogen chloride is bubbled in to saturation and the resulting solution is stoppered and kept cold for 20 minutes and then at ambient temperature for 40 minutes. The reaction mixture is then concentrated in vacuo to give 8.4 g. of crude product. Recrystallization from hot isopropanol yields 5.2 g. of 3-[(phenylmethoxy)methyl]-L-histidine, methyl ester, dihydrochloride; m.p. 159°–160°, resolidified at m.p. 209°–210°. $[\alpha]_D = +13.4°$ (c=1.11, methanol).

(b) N-[N-[(1,1-Dimethylethoxy)carbonyl]-L-phenylalanyl]-3-[(phenylmethoxy)methyl]-L-histidine, methyl ester Dicyclohexylcarbodiimide (2.17 g., 10.5 mmole) is added to a mixture of 3-[(phenylmethoxy)methyl]-L-histidine, methyl ester, dihydrochloride (3.62 g., 10 mmole), N-[(1,1-dimethylethoxy)carbonyl]-L-phenylalanine (2.56 g., 10 mmole), and hydroxybenzotriazole hydrate (1.68 g., 11 mmole) in dimethylformamide (70 ml.) cooled in an ice-water bath under nitrogen followed by the addition of N-methylmorpholine (2.02 g., 20 mmole). The reaction is allowed to warm to room temperature overnight, then chilled for 15 minutes in an ice-bath after diluting with 200 ml. of ethyl acetate. The cold solution is filtered and the filtrate is washed with three 70 ml. portions of water, saturated sodium bicarbonate and brine, dried (MgSO$_4$), and concentrated in vacuo to give 4.9 g. of crude product. Flash chromatography on 250 g. of LPS-1 silica gel eluting with 3 column volumes of 1:1 chloroform:ethyl acetate followed by a gradient to 15:1 chloroform:methanol yields 4.2 g. of purified product. Recrystallization from hot ethyl acetate affords 3.7 g. of N-[N-[(1,1-dimethylethoxy)carbonyl]-L-phenylalanyl]-3-[(phenylmethoxy)methyl]-L-histidine, methyl ester; m.p. 165°–166°; $[\alpha]_D = -15.4°$ (c=0.5, methanol). TLC (silica gel; chloroform:methanol 12:1) $R_f = 0.40$.

(c) N-[N-[(1,1-Dimethylethoxy)carbonyl]-L-phenylalanyl]-3-[(phenylmethoxy)methyl]-L-histidine 1N Aqueous sodium hydroxide (6.8 ml.) is added to a solution of N-[N-[(1,1-dimethylethoxy)carbonyl]-L-phenylalanyl]-3-[(phenylmethoxy)methyl]-L-histidine, methyl ester (3.3 g., 6.1 mmole) in methanol (18 ml.). After 3 hours, the reaction is diluted with water (42 ml.) and then concentrated in vacuo to remove most of the methanol. The resulting solution is rinsed with 25 ml. of ether and then acidified to pH of 4.5 using 1N hydrochloric acid. The precipitated solid is filtered, washed with water, and dried in vacuo to give 2.95 g. of N-[N-[(1,1-dimethylethoxy)carbonyl]-L-phenylalanyl]-3-[(phenylmethoxy)methyl]-L-histidine; m.p. 189°–190° (dec.); $[\alpha]_D = -5.7°$ (c=1, dimethylformamide). TLC (silica gel; 2% NH$_4$OH in n-propanol) $R_f = 0.36$.

(d) [(Phenylmethoxy)carbonyl]-L-leucine, 2-(trimethylsilyl)ethyl ester

A mixture of [(phenylmethoxy)carbonyl]-L-leucine (20.1 g., 75.7 mmole), dimethylaminopyridine (0.925 g., 7.57 mmole), and 2-(trimethylsilyl)ethanol (8.95 g., 75.7 mmole) in methylene chloride (200 ml.) is cooled in an ice-bath under nitrogen and treated with a solution of dicyclohexylcarbodiimide (15.6 g., 75.7 mmole) in 50 ml. of methylene chloride. The ice-bath is removed after 20 minutes and the reaction is allowed to come to room temperature overnight. The reaction mixture is filtered, concentrated in vacuo and partitioned between 800 ml. of ether and 200 ml. of water. The organic layer is separated and further rinsed with saturated sodium bicarbonate, water, 10% potassium bisulfate, water, and brine, dried (MgSO$_4$), and concentrated in vacuo to give 26.1 g. of crude product. Flash filtration over silica gel (180 g. in 20:1 hexane:ethyl acetate) yields 22.9 g. of crude product which is chromatographed using the Waters Prep 500 LC, two columns eluted with 15:1 hexane:ethyl acetate (250 ml./minute, 200 ml. fractions). Combining the pure product fractions yields 19.6 g. of [(phenylmethoxy)carbonyl]-L-leucine, 2-(trimethylsilyl)ethyl ester as an oil; $[\alpha]_D = -7.3°$ (c=1, chloroform). TLC (silica gel; 10:1 hexane:ethyl acetate) $R_f = 0.12$.

(e) L-Leucine, 2-(trimethylsilyl)ethyl ester 1 g. of 10% palladium on carbon catalyst is added to a solution of [(phenylmethoxy)carbonyl]-L-leucine, 2-(trimethylsilyl)ethyl ester (9.1 g., 24.9 mmole) in ethyl acetate (200 ml.) cooled in an ice-bath under nitrogen. The reaction mixture is subjected to a steady stream of hydrogen gas for 2.5 hours at room temperature, then filtered and concentrated in vacuo to remove volatiles and yield 5.8 g. of L-leucine, 2-(trimethylsilyl)ethyl ester as a liquid product. TLC (silica gel, 3:1 hexane:ethyl acetate) $R_f = 0.08$.

(f) [(S)-1-Chloro-5-methyl-2-oxo-3-hexyl]carbamic acid, 1,1-dimethylethyl ester N-Methyl-N'-nitro-N-nitrosoguanidine (24.2 g., 165 mmole) is added portionwise over a period of 30 minutes to a mixture of ether (275 ml.) and 40% aqueous potassium hydroxide (75 ml.) in a 1 l. Erlenmeyer flask cooled in a ice-water bath. Throughout the reaction the flask is magnetically stirred and loosely stoppered. At the end of the addition, the reaction is stirred cold for 45 minutes longer.

A solution of [(1,1-dimethylethoxy)carbonyl]-L-leucine hydrate (19.2 g., 77 mmole) in dry tetrahydrofuran (180 ml.) is cooled to −10° to −15° under an atmosphere of argon. The reaction mixture is treated with N-methylmorpholine (7.79 g., 77 mmole), added neat, followed by the careful addition of isobutylchloroformate (10.5 g., 77 mmole), added neat and dropwise while keeping the temperature between −10° and −15°. Upon completion of the addition, the solution is kept at −15°.

As much as possible of the diazomethane solution in ether is decanted into a 1 l. Erlenmeyer flask and kept cold. The remainder is poured into a 500 ml. separatory funnel. The aqueous layer is drained and discarded while the ether is added to the decanted material. The total ethereal diazomethane is quickly dried over solid potassium hydroxide, then decanted into a 1 l. filtering flask fitted with an argon sidearm connection, magnetically stirred and cooled in a −10° bath. Total volume by now is about 400 ml. A filtering funnel is put in place with vacuum momentarily connected at sidearm, the mixed anhydride preparation is quickly filtered directly into the −10° ethereal diazomethane. Ether rinses are used to finish the transfer. The vacuum is replaced by the argon line and the reaction is allowed to warm to 0° and is kept at 0° for one hour. The flask is then stoppered, fitted with a balloon and refrigerated overnight.

The reaction mixture is next rinsed with 400 ml. each of 3% aqueous acetic acid, water, saturated sodium bicarbonate, water, and brine, dried (MgSO$_4$) and concentrated in vacuo. The crude product is recrystallized from ether-petroleum ether to give 17.2 g. of [(S)-1-chloro-5-methyl-2-oxo-3-hexyl]carbamic acid, 1,1-dimethylethyl ester; m.p. 87°–89°; $[\alpha]_D = -51.2°$ (c=1, methylene chloride).

Calculated for C$_{12}$H$_{21}$N$_3$O$_3$: C, 56.45; H, 8.29; N, 16.46. Found: C, 56.13; H, 8.31; N, 16.39.

(g)
N-[(S)-3-[[(1,1-Dimethylethoxy)carbonyl]amino]-5-methyl-2-oxohexyl]-L-leucine, 2-(trimethylsilyl)ethyl ester A solution of [(S)-1-chloro-5-methyl-2-oxo-3-hexyl]-carbamic acid, 1,1-dimethylethyl ester (3.55 g., 13.5 mmole) in dimethylformamide (18 ml.) is added, in one portion, to a mixture of L-leucine, 2-(trimethylsilyl)ethyl ester (5.47 g., 23.6 mmole), sodium iodide (1.06 g., 7.1 mmole), and sodium bicarbonate (2.0 g., 23.6 mmole) in dimethylformamide (18 ml.). The reaction, under an atmosphere of nitrogen, is stirred at ambient temperature overnight, then diluted with 500 ml. of 1:1 ethyl acetate:ether and washed with 100 ml. portions of water, 5% sodium bicarbonate, water, and brine, dried (MgSO$_4$) and concentrated in vacuo to give 7.8 g. of crude product. Flash chromatography on 85 g. of LPS-1 silica gel eluting with 10:1 hexane:ethyl acetate yields 5.0 g. of N-[(S)-3-[[(1,1-dimethylethoxy)carbonyl]amino]-5-methyl-2-oxohexyl]-L-leucine, 2-(trimethylsilyl)ethyl ester as an oil; $[\alpha]_D = -15.5°$ (c=1, chloroform. TLC (silica gel; 6:1 hexane:ethyl acetate) R$_f$=0.11.

(h)
N-[(S)-3-[[(1,1-Dimethylethoxy)carbonyl]amino]-5-methyl-2-hydroxyhexyl]-L-leucine, 2-(trimethylsilyl)ethyl ester Sodium borohydride (2.1 g., 54.5 mmole) is added to a solution of N-[(S)-3-[[(1,1-dimethylethoxy)carbonyl]amino]-5-methyl-2-oxohexyl]-L-leucine, 2-(trimethylsilyl)ethyl ester (5.0 g., 10.9 mmole) in a mixture of tetrahydrofuran (150 ml.) and water (50 ml.) cooled in an ice-water bath. After 5 minutes the reaction is poured into water (300 ml.) and extracted with ethyl acetate (600 ml.). The organic extract is rinsed further with water and brine, dried (MgSO$_4$) and concentrated in vacuo to yield 4.7 g. of crude product. Flash chromatography on 140 g. of LPS-1 silica gel eluting with 10:1 petroleum ether:acetone yields 3.5 g. of N-[(S)-3-[[(1,1-dimethylethoxy)carbonyl]amino]-5-methyl-2-hydroxyhexyl]-L-leucine, 2-(trimethylsilyl)ethyl ester as an oil; $[\alpha]_D = -27.8°$; (c=1, chloroform). TLC (silica gel; 10:1 petroleum ether:acetone) R$_f$=0.20.

(i)
N-[(S)-3-[[(1,1-Dimethylethoxy)carbonyl]amino]-5-methyl-2-hydroxyhexyl]-N-[(phenylmethoxy)carbonyl]-L-leucine, 2-(trimethylsilyl)ethyl ester A mixture of N[(S)-3-[[(1,1-dimethylethoxy)carbonyl]amino]-5-methyl-2-hydroxyhexyl]-L-leucine, 2-(trimethylsilyl)ethyl ester (3.5 g., 7.6 mmole) and N-[(phenylmethoxy)carbonyloxy]succinimide (2.8 g., 11.4 mmole) in dry tetrahydrofuran (13.5 ml.) is stirred under nitrogen in a stoppered flask at ambient temperature for 48 hours, then diluted with 100 ml. of ether and rinsed with water and brine, dried (MgSO$_4$) and concentrated in vacuo to give 5.6 g. of crude product. The mixture is flash filtered through 60 g. of LPS-1 silica gel eluting with 20:1 petroleum ether:acetone to give 4.3 g. of N-[(S)-3-[[(1,1-dimethylethoxy)carbonyl]amino]-5-methyl-2-hydroxyhexyl]-N-[(phenylmethoxy)carbonyl]-L-leucine, 2-(trimethylsilyl)ethyl ester as a mixture of isomers.

(j)
N-[[(3S)-3-[(1,1-Dimethylethoxy)carbonyl]-2,2-dimethyl-4-(2-methylpropyl)oxazolidin-5-yl]methyl]-N-[(phenylmethoxy)carbonyl]-L-leucine, 2-(trimethylsilyl)ethyl ester N-[(S)-3-[[(1,1-Dimethylethoxy)carbonyl]amino]-5-methyl-2-hydroxyhexyl]-N-[(phenylmethoxy)carbonyl]-L-leucine, 2-(trimethylsilyl)ethyl ester (1.9 g., 3.2 mmole) is dissolved in dry methylene chloride (7 ml.) and treated with 2-methoxypropene (0.690 g., 9.6 mmole) followed by pyridinium-p-toluene-sulfonic acid. The reaction is stirred at room temperature under nitrogen for five hours and then diluted with 500 ml. of ether and rinsed with two 75 ml. portions of water and 75 ml. of brine, dried (MgSO$_4$), and concentrated in vacuo to give the crude product. Flash chromatography on 100 g. of LPS-1 silica gel eluting with a gradient from 100:1 to 25:1 petroleum ether:acetone gives 1.9 g. of N-[[(3S)-3-[(1,1-dimethylethoxy)carbonyl]-2,2-dimethyl-4-(2-methylpropyl)oxazolidin-5-yl]methyl]-N-[(phenylmethoxy)carbonyl]-L-leucine, 2-(trimethylsilyl)ethyl ester.

(k)
N$^2$-[[(3S)-3-[(1,1-Dimethylethoxy)carbonyl]-2,2-dimethyl-4-(2-methylpropyl)oxozolidin-5-yl]methyl]-N-[(phenylmethoxy)carbonyl]-N-[2-(2-pyridinyl)ethyl]-L-leucinamide A solution of the 2-(trimethylsilyl)ethyl ester product from part (j) (940 mg., 1.48 mmole) in dimethylformamide (11 ml.) at room temperature under argon is treated with tetra n-butyl ammonium fluoride trihydrate (934 mg., 2.96 mmole). After 15 minutes, the reaction is worked up by diluting with ether (50 ml.) and ethyl acetate (50 ml.), rinsed with three 25 ml. portions of water, rinsed with brine, dried (MgSO$_4$), and concentrated in vacuo to give 765 mg. of the free acid intermediate.

A solution of this free acid (390 mg., 0.729 mmole), hydroxybenzotriazole hydrate 112 mg., 0.729 mmole) and 2-(2-aminoethyl)pyridine (98 mg., 0.802 mmole) in dimethylformamide (7 ml.) is cooled in an ice-water bath under argon and treated with dicyclohexylcarbodiimide (158 mg., 0.765 mmole). The reaction is allowed to come to room temperature overnight, then diluted with 30 ml. of ethyl acetate and chilled in an ice-water bath for 15 minutes. The chilled mixture is then filtered and diluted with 30 ml. of ether. The organic solution is rinsed with three 10 ml. portions of water and 10 ml. of brine, dried (MgSO$_4$) and concentrated in vacuo to give 539 mg. of crude product. Flash chromatography on 42 g. LPS-1 silica gel packed in chloroform and eluted with 20:1 chloroform:methanol yields partially purified product. Rechromatography on 40 g. of LPS-1 silica gel packed in 1:1 chloroform:hexanes and eluted with a gradient of 100:1 to 20:1 chloroform:methanol yields 422 mg. of N$^2$-[[(3S)-3-[(1,1-dimethylethoxy)carbonyl]-2,2-dimethyl-4-(2-methylpropyl)oxazolidin-5-yl]methyl]-N-[(phenylmethoxy)carbonyl]-N-[2-(2-pyridinyl)ethyl]-L-leucinamide. TLC (silica gel, 10:1 chloroform:methanol) R$_f$=0.47.

(l)
N$^2$-[3-[[N-[N-[(1,1-Dimethylethoxy)carbonyl]-L-phenylalanyl]-3-[(phenylmethoxy)methyl]-L-histidyl]amino]-2-hydroxy-5-methylhexyl]-N-[(phenylmethoxy)carbonyl]-N-[2-(2-pyridinyl)ethyl]-L-leucinamide A solution of N$^2$-[[(3S)-3-[(1,1-dimethylethoxy)carbonyl]-2,2-dimethyl-4-(2-methylpropyl)oxazolidin-5-yl]methyl]-N-[(phenylmethoxy)carbonyl]-N-[2-(2-pyridinyl)ethyl]-L-leucinamide (422 mg., 0.660 mmole) in methylene chloride (3 ml.) is cooled in an ice-water bath and treated with trifluoroacetic acid (6 ml.). The bath is removed and the stoppered reaction is stirred for one hour at ambient temperature, then concentrated in vacuo and treated with tetrahydrofuran (8 ml.) and 1N hydrochloric acid (3 ml.). After 4 hours, the reaction is basified with 15 ml. of saturated aqueous sodium bicarbonate amd extracted with two 30 ml. portions of chloroform. The combined organic extracts are rinsed with brine, dried (MgSO$_4$) and concentrated in vacuo to yield 329 mg. of free amine.

Dicyclohexylcarbodiimide (134 mg., 0.671 mmole) is added to a mixture of the above amine (0.620 mmole), hydroxybenzotriazole hydrate (104 mg., 0.682 mmole) and N-[N-[(1,1-dimethylethoxy)carbonyl]-L-phenylalanyl]-3-[(phenylmethoxy)methyl]-L-histidine (324 mg., 0.620 mmole) chilled in an ice-water bath under argon. The reaction is kept in a refrigerator overnight, then diluted with 30 ml. of ethyl acetate, chilled in an ice-bath for 15 minutes, then filtered and diluted with more ethyl acetate. The organic extract is rinsed with 10 ml. each of water, saturated aqueous sodium bicarbonate and brine, dried (MgSO$_4$), and concentrated in vacuo to 730 mg. of crude product. Flash chromatography on 45 g. of LPS-1 silica gel eluting with 2 column volumes of 2:1 chloroform:ethyl acetate followed by 20:1 chloroform:methanol yields 583 mg. of N$^2$-[3-[[N-[N-[(1,1-dimethylethoxy)carbonyl]-L-phenylalanyl]-3-[(phenylmethoxy)methyl]-L-distidyl]amino]-2-hydroxy-5-methylhexyl]-N-[(phenylmethoxy)carbonyl]-N-[2-(2-pyridinyl)ethyl]-L-leucinamide; [α]$_D$=−31.9° (c=1, chloroform).
TLC (silica gel, 10:1 chloroform:methanol) R$_f$=0.38.
Anal. calc'd. for C$_{56}$H$_{74}$N$_8$O$_9$: C, 67.04; H, 7.77; N, 11.17. Found: C, 66.48; H, 7.55; N, 11.29.

(m)
N$^2$-[3-[[N-[N-[(1,1-Dimethylethoxy)carbonyl]-L-phenylalanyl]-L-histidyl]amino]-2-hydroxy-5-methylhexyl]-N-[2-(2-pyridinyl)ethyl]-L-leucinamide, acetic acid salt (1:2)

To a solution of the product from part (1) (558 mg., 0.556 mmole) in methanol (25 ml.) is added 5 ml. of water, 1.78 ml. of 1N hydrochloric acid, and 90 mg. of 20% palladium hydroxide on carbon catalyst. The mixture is hydrogenated at 1 atmosphere of hydrogen using a balloon for 16 hours, then retreated with 90 mg. of fresh catalyst for 6 more hours to completion. The reaction mixture is filtered, concentrated in vacuo, and the product is partitioned between 60 ml. of chloroform and 20 ml. of saturated sodium bicarbonate. Some ether is added to separate the layers and the organic extract is rinsed with brine, dried (MgSO$_4$), and concentrated in vacuo to afford crude product. Flash chromatography on 45 g. of LPS-1 silica gel eluting with 90:20:2.5:1 chloroform:methanol:water:acetic acid gives 342 mg. of N$^2$-[3-[[N-[N-[(1,1-dimethylethoxy)carbonyl]-L-phenylalanyl]-L-histidyl]amino]-2-hydroxy-5-methylhexyl]-N-[2-(2-pyridinyl)ethyl]-L-leucinamide, acetic acid salt (1:2); m.p. 70°–82°; [α]$_D$=−16.6° (c=0.5, methanol). TLC (silica gel, 90:20:2.5:1 chloroform:methanol:water:acetic acid) R$_f$=0.29.
Anal. calc'd for C$_{40}$H$_{60}$N$_8$O$_6$.2C$_2$H$_4$O$_2$.1.6H$_2$O: C, 58.85; H, 7.99; N, 12.48. Found: C, 58.81; H, 7.85; N, 12.50.

EXAMPLE 2

(2R,3S)-[3-[[N-[(1,1-Dimethylethoxy)carbonyl]-L-phenylalanyl-L-histidyl]amino]-2-hydroxy-5-methylhexyl]-L-leucinamide, diacetate salt (a) (2R, 3S)- and (2S,3S)-N-[3-[[(1,1-Dimethylethoxy)carbonyl]amino]-5-methyl-2-hydroxyhexyl]-N-[(phenylmethoxy)carbonyl]-L-leucine, 2-(trimethylsilyl)ethyl ester The mixture of isomers obtained in Example 1(i) is separated on a Waters Prep 500 LC using two columns eluted with 25:1 petroleum ether:acetone (250 ml./min., 200 ml. fractions). Homogeneous fractions of the first isomer eluted are pooled to give 1.53 g. of (2S, 3S)-N-[3-[[(1,1-dimethylethoxy)carbonyl]amino]-5-methyl-2-hydroxyhexyl]-N-[(phenylmethoxy)carbonyl]-L-leucine, 2-(trimethylsilyl)ethyl ester; [α]$_D$=−57.4° (c=1, chloroform). TLC (silica gel, 10:1 petroleum ether:acetone) R$_f$=0.24.
Anal. calc'd. for C$_{31}$H$_{54}$N$_2$O$_7$Si: C, 62.59; H, 9.15; N, 4.71. Found: C, 62.57; H, 8.87; N, 4.99.

After collecting 132 mg. of a mixture fraction, 1.72 g. of pure (2R, 3S)-N-[3-[[(1,1-dimethylethoxy)carbonyl]amino]-5-methyl-2-hydroxyhexyl]-N-[(phenylmethoxy)carbonyl]-L-leucine, 2-(trimethylsilyl)ethyl ester is obtained as an oil; [α]$_D$=−25.2° (c=1, chloroform). TLC (silica gel, 10:1 petroleum ether:acetone) R$_f$=0.21
Anal. calc'd. for C$_{31}$H$_{54}$N$_2$O$_7$Si: C, 62.59; H, 9.15; N, 4.71. Found: C, 62.29; H, 9.28; N, 4.62.

(b) (2R, 3S)-N-[[3-[(1,1-Dimethylethoxy)carbonyl]-2,2-dimethyl-4-(2-methylpropyl)oxazolidin-5-yl]methyl]-N-[(phenylmethoxy)carbonyl]-L-leucine, 2-(trimethylsilyl)ethyl ester The (2R, 3S) isomer product from part (a) (2.42 g., 4.1 mmole) is dissolved in 72 ml. of dry methylene chloride and treated with 2-methoxypropene (5.9 g., 82 mmole), followed by pyridinium-p-toluenesulfonic acid (0.206 g., 0.802 mmole). The reaction is stirred under nitrogen at room temperature for one hour and then diluted with ether (500 ml.) and rinsed with water and brine, dried (MgSO$_4$), and concentrated in vacuo to give 3.1 g. of crude product. Chromatography on a Waters Prep 500 LS using two columns eluted with 35:1 petroleum ether:acetone (250 ml./min., 125 ml. fractions) yields 2.2 g. of (2R, 3S)-N-[[3-[(1,1-dimethylethoxy)carbonyl]-2,2-dimethyl-4-(2-methylpropyl)oxazolidin-5-yl]methyl]-N-[(phenylmethoxy)carbonyl]-L-leucine, 2-(trimethylsilyl)ethyl ester as an oil; $[\alpha]_D = -4.3°$ (c=1, chloroform). TLC (silica gel, 15:1 petroleum ether:acetone) R$_f$=0.44.

Anal. calc'd. for C$_{34}$H$_{58}$N$_2$O$_7$Si: C, 64.32; H, 9.21; N, 4.41. Found: C, 64.39; H, 9.40; N, 4.25.

(c) (2R, 3S)-N-[[3-[(1,1-Dimethylethoxy)carbonyl]-2,2-dimethyl-4S-(2-methylpropyl)oxazolidin-5-yl]methyl]-N-[(phenylmethoxy)carbonyl]-L-leucinamide A solution of the 2-(trimethylsilyl)ethyl ester product from part (b) (1.3 g., 2.05 mmole) in dimethylformamide (17 ml.) is treated with tetra n-butyl ammonium fluoride trihydrate (678 mg., 2.15 mmole), and the reaction is stirred at ambient temperature for 90 minutes. The reaction is cooled to $-20°$ under nitrogen, then treated with isobutylchloroformate (279 μl, 2.15 mmole) and kept at $-15°$ for 15 minutes. The reaction is then treated with 6N ammonia/methanol (1.1 ml., 6.60 mmole), kept at 0° for several minutes, and then allowed to warm to ambient temperature. After one hour, the reaction is worked up by treating with 150 ml. of water, extracted with 3×300 ml. of a 1:1 mixture of ethyl acetate:ethyl ether, dried, and concentrated in vacuo to give 1.1 g. of crude product. Flash chromatography on 110 g. of LPS-1 silica gel eluting with 5% acetone in petroleum ether separates out starting material and eluting with 10% acetone in petroleum ether gives the product. The product containing fractions are pooled to give 635 mg. of (2R, 3S)-N-[[3-(1,1-dimethylethoxy)carbonyl]-2,2-dimethyl-4S-(2-methylpropyl)oxazolidin-5-yl]methyl]-N-[(phenylmethoxy)carbonyl]-L-leucinamide; $[\alpha]_D = +4.9°$ (c=1, chloroform). TLC (silica gel, 1:1 petroleum ether:acetone) R$_f$=0.65.

Anal. calc'd. for C$_{29}$H$_{47}$N$_3$O$_6$: C, 65.26; H, 8.88; N, 7.87. Found: C, 65.10; H, 8.87; N, 7.63.

(d) (2R, 3S)-3-[[N-[(1,1-Dimethylethoxy)carbonyl]-L-phenylalanyl-N-[(phenylmethoxy)methyl]-L-histidyl]amino]-2-hydroxy-5-methylhexyl]-N-[(phenylmethoxy)carbonyl]-L-leucinamide A solution of the amide product from part (c) (349 mg., 0.65 mmole) in dry methylene chloride (3.6 ml.) is cooled in an ice-water bath under nitrogen and treated with trifluoroacetic acid (1.8 ml.). The stoppered reaction is stirred at room temperature for 1.5 hours, then concentrated in vacuo and treated with tetrahydrofuran (3 ml.) and 1N aqueous hydrochloric acid (1.4 ml.). After 3 hours at room temperature, the reaction is treated with 10 ml. of saturated sodium bicarbonate and extracted with two 20 ml. portions of chloroform. The combined organic extracts are rinsed with brine, dried (MgSO$_4$), and concentrated in vacuo to give 270 mg. of the amino alcohol.

Dicyclohexylcarbodiimide (140 mg., 0.68 mmole) is added to a mixture of the above amino alcohol (0.65 mmole), hydroxybenzotriazole hydrate (99 mg., 0.65 mmole), and N-[N-[(1,1-dimethylethoxy)carbonyl]-L-phenylalanyl]-3-[(phenylmethoxy)methyl]-L-histidine (340 mg., 0.65 mmole) in dimethylformamide (5 ml.) cooled in an ice-water bath under nitrogen. The reaction is allowed to warm to room temperature overnight, then diluted with 40 ml. of ethyl acetate and 10 ml. of ether and filtered. The extract is washed with 10 ml. portions of 5% potassium bisulfate, water, saturated sodium bicarbonate, water, and brine, dried (MgSO$_4$), and concentrated in vacuo to give 558 mg. of crude product. Flash chromatography on 35 g. of LPS-1 silica gel eluting with a gradient of 2:1 chloroform:ethyl acetate to 20:1 chloroform:methanol yields 232 mg. of (2R, 3S)-[3-[[N-[(1,1-dimethylethoxy)carbonyl]-L-phenylalanyl-N-[(phenylmethoxy)methyl]-L-histidyl]amino]-2-hydroxy-5-methylhexyl]-N-[(phenylmethoxy)carbonyl]-L-leucinamide; m.p. 92°–100°; $[\alpha]_D = -31.8°$ (c=1, chloroform). TLC (silica gel, 10:1 chloroform: methanol) R$_f$=0.31.

(e) (2R, 3S)-[3-[[N-[(1,1-Dimethylethoxy)carbonyl]-L-phenylalanyl-L-histidyl]amino]-2-hydroxy-5-methylhexyl]-L-leucinamide, diacetate salt A mixture of the product from part (d) (220 mg., 0.245 mmole), 20% palladium hydroxide on carbon catalyst (75 mg.), methanol (11 ml.), water (2.2 ml.) and 1N aqueous hydrochloric acid (0.54 ml.) is hydrogenated at 1 atmosphere for 20 hours. The reaction is filtered, concentrated in vacuo to 180 mg. of crude product, and flash chromatographed on 30 g. of LPS-1 silica gel eluting with 100:20:2.5:1 chloroform:methanol:water:acetic acid to give 94 mg. of (2R, 3S)-[3-[[N-[(1,1-dimethylethoxy)carbonyl]-L-phenylalanyl-L-histidyl]amino]-2-hydroxy-5-methylhexyl]-L-leucinamide, diacetate salt; m.p. 95°–99°, then 161°–164° (dec.); $[\alpha]_D = 12.6°$ (c=0.5, methanol). TLC (silica gel; 90:20:2.5:1 chloroform:methanol:water:acetic acid) R$_f$=0.23.

Anal. calc'd. for C$_{33}$H$_{53}$N$_7$O$_6$.2C$_2$H$_4$O$_2$.2.3H$_2$O: C, 55.18; H, 8.21; N, 12.18. Found: C, 54.98; H, 7.84; N, 12.22.

EXAMPLE 3

N-[(3S)-3-[[N-[(1,1-Dimethylethoxy)carbonyl]-3-[(phenylmethoxy)methyl]-L-histidyl]amino]-2-hydroxy-5-methylhexyl]-L-leucinamide, diacetate salt

(a) N-[[(3S)-3-[(1,1-Dimethylethoxy)carbonyl]-2,2-dimethyl-4-(2-methylpropyl)oxazolidin-5-yl]methyl]-N-[(phenylmethoxy)carbonyl]-L-leucinamide A solution of N-[[(3S)-3-[(1,1-dimethylethoxy)carbonyl]-2,2-dimethyl-4-(2-methylpropyl)oxazolidine-5-yl]methyl]-N-[(phenylmethoxy)carbonyl]-L-leucine, 2-(trimethylsilyl)ethyl ester (379 mg., 0.597 mmole), from Example 1(j), in dimethylformamide (4 ml.) is treated with tetra-n-butyl ammonium fluoride trihydrate (414 mg., 1.31 mmole) at room temperature under argon. After 3 hours the reaction mixture is taken up in 25 ml. of ethyl acetate and 25 ml. of ether. The organic extract is rinsed with three 10 ml. portions of water, brine, dried (MgSO$_4$), and concentrated in vacuo to give 450 mg. of crude carboxylic acid.

The above carboxylic acid (0.597 mmole) is dissolved in dry tetrahydrofuran (1.8 ml.) and cooled to $-25°$ under argon. N-methylmorpholine (60.4 g., 0.597 mmole) is added followed by the slow, careful addition of isobutylchloroformate (81.5 mg., 0.597 mmole). After 5 minutes 7N methanolic ammonia (0.358 ml., 2.51 mmole) is slowly added dropwise. The external bath temperature is allowed to warm to $-10°$ over a period of 30 minutes, then the reaction is stoppered and left in a refrigerator overnight. The reaction is next diluted with 60 ml. of 1:1 ethyl acetate:ether and rinsed with two 10 ml. portions of water, 10 ml. of 5% potassium bisulfate, water and brine, dried (MgSO$_4$), and concentrated in vacuo to give 500 mg. of crude product. Flash chromatography on 30 g. of LPS-1 silica gel eluting initially with 3 column volumes of chloroform, followed by 30:1 chloroform:methanol yields 313 mg. of N-[[(3S)-3-[(1,1-dimethylethoxy)carbonyl]-2,2-dimethyl-4-(2-methylpropyl)oxazolidin-5-yl]methyl]-N-[(phenylmethoxy)carbonyl]-L-leucinamide. TLC (silica gel, 20:1 chloroform:methanol) R$_f$=0.48, 0.54.

(b)

N-[(3S)-3-[[N-[1,1-Dimethylethoxy)carbonyl]-3-[(phenylmethoxy)methyl]-L-histidyl]amino]-2-hydroxy-5-methylhexyl]-N$^2$-[(phenylmethoxy)carbonyl]-L-leucinamide The amide product from part (a) (310 mg., 0.581 mmole) is dissolved in 6 ml. of dry methylene chloride cooled in an ice-water bath under argon and 3 ml. of trifluoroacetic acid is added. After one hour at ice-water bath temperature, the reaction is concentrated in vacuo and treated with 6 ml. of tetrahydrofuran and 3 ml. of 1N aqueous hydrochloric acid. After 5 hours at room temperature, the reaction is treated with 15 ml. of saturated sodium bicarbonate and extracted with two 20 ml. portions of chloroform. The organic extract is rinsed with brine, dried (MgSO$_4$), and concentrated in vacuo to give 253 mg. of aminoalcohol.

Dicyclohexylcarbodiimide (126 mg., 0.610 mmole) is added to a mixture of the above aminoalcohol (0.581 mmole), hydroxybenzotriazole hydrate (97.8 mg., 0.639 mmole), and N-[(1,1-dimethylethoxy)carbonyl]-3-[(phenylmethoxy)methyl]-L-histidine (218 mg., 0.581 mmole) [prepared according to the procedure of Brown et al., J. Chem.Soc.Perkins Trans., Vol. 1, p. 2261 (1979)] in dimethylformamide (5 ml.) in an ice-bath under argon. The reaction is allowed to warm to room temperature overnight. It is then diluted with 30 ml. of ethyl acetate, chilled in an ice-bath for 30 minutes, then filtered, then diluted with an additional 30 ml. of ether, and rinsed with two 10 ml. portions of water, two 10 ml. portions of saturated sodium bicarbonate, water, and brine, dried (MgSO$_4$) and concentrated in vacuo to 438 mg. of crude product. Flash chromatography on 25 g. of LPS-1 silica gel eluting with two column volumes of 3:2 chloroform: ethyl acetate followed by 15:1 chloroform:methanol yields 270 mg. of N-[(3S)-3-[[N-[(1,1-dimethylethoxy)carbonyl]-3-[(phenylmethoxy)methyl]-L-histidyl]amino]-2-hydroxy-5-methylhexyl]-N$^2$-[(phenylmethoxy)carbonyl]-L-leucinamide as a 0.7 water solvate; m.p. 75°–98°; [α]$_D$=−58.6° (c=1, chloroform). TLC (silica gel, 15:1 chloroform:methanol) R$_f$=0.26.

(c)

N-[(3S)-3-[[N-[(1,1-Dimethylethoxy)carbonyl]-3-[(phenylmethoxy)methyl]-L-histidyl]amino]-2-hydroxy-5-methylhexyl]-L-leucinamide, diacetate salt A mixture of the product from part (b) (260 mg., 0.340 mmole), methanol (6 ml.), water (0.4 ml.), acetic acid (1.2 ml.), and 10% palladium on carbon catalyst (75 mg.) is hydrogenated at 1 atmosphere for two hours. The reaction is then filtered, concentrated in vacuo, and flash chromatographed on 25 g. of LPS-1 silica gel eluting with 100:20:2.5:1 chloroform:methanol:water:acetic acid to give 186 mg. of N-[(3S)-3-[[N-[(1,1-dimethylethoxy)carbonyl]-3-[(phenylmethoxy)methyl]-L-histidyl]amino]-2-hydroxy-5-methylhexyl]-L-leucinamide, diacetate salt; m.p. 109°–123°; [α]$_D$=−28.6° (c=0.5, methanol). TLC (silica gel; 90:20:2.5:1 chloroform:methanol:water:acetic acid) R$_f$=0.30.

Anal. calc'd. for C$_{32}$H$_{52}$N$_6$O$_6$.2C$_2$H$_4$O$_2$.1.2H$_2$O C, 57.01; H, 8.29; N, 11.08. Found: C, 57.05; H, 8.08; N, 10.91.

EXAMPLE 4

N-[(3S)-3-[[N-[(1,1-Dimethylethoxy)carbonyl]-L-histidyl]amino]-2-hydroxy-5-methylhexyl]-L-leucinamide, acetate salt 20% Palladium hydroxide on carbon catalyst (10 ml.) is added to N-[(3S)-3-[[N-[(1,1-dimethylethoxy)carbonyl]-3-[(phenylmethoxy)methyl]-L-histidyl]amino]-2-hydroxy-5-methylhexyl]-L-leucinamide, diacetate (148 mg., 0.195 mmole) dissolved in a mixture of methanol (10 ml.), water (2.1 ml.), and 1N aqueous hydrochloric acid (0.429 ml.). The mixture is kept under 1 atmosphere of hydrogen for 18 hours. Two flash chromatographies on 20–25 g. LPS-1 silica gel eluting with 90:20:2.5:1 chloroform:methanol:water:acetic acid remove byproduct. Product fractions are pooled and triturated with ether to give 83 mg. of acetate salt. This product is dissolved in aqueous methanol and filtered through a polycarbonate millipore filtration device. Removal of solvents in vacuo yields 75 mg. of triturated salt. This material is partitioned between chloroform and saturated aqueous sodium bicarbonate. After drying (Na$_2$SO$_4$ and MgSO$_4$), the chloroform extract is treated with acetic acid (0.2 ml.) and concentrated in vacuo to yield 60 mg. of N-[(3S)-3-[[N-[(1,1-dimethylethoxy)carbonyl]-L-histidyl]amino]-2-hydroxy-5-methylhexyl]-L-leucinamide, acetate salt; m.p. 66°–74°; [α]$_D$=−36.4° (c=0.5, methanol). TLC (silica gel, 90:20:2.5:1 chloroform:methanol:water:acetic acid) R$_f$=0.16.

Anal. calc'd for C$_{24}$H$_{44}$N$_6$O$_5$.1.6C$_2$H$_4$O$_2$.0.8H$_2$O: C, 53.80; H, 8.63; N, 13.84 Found: C, 53.84; H, 8.49; N, 13.84.

EXAMPLE 5

(2S, 3S)-[3-[[N-[(1,1-Dimethylethoxy)carbonyl]-L-phenylalanyl-L-histidyl]amino]-2-hydroxy-5-methylhexyl]-L-leucinamide, diacetate salt

(a) (2S, 3S)-N-[[3-[(1,1-Dimethylethoxy)carbonyl]-2,2-dimethyl-4-(2-methylpropyl)oxazolidin-5-yl]methyl]-N-[(phenylmethoxy)carbonyl]-L-leucine, 2-(trimethylsilyl)ethyl ester 2-Methoxypropene (3.49 g., 48.4 mmole) is added to a solution of (2S, 3S)-N-[3-[[(1,1-dimethylethoxy)carbonyl]amino]-5-methyl-2-hydroxyhexyl]-N-[(phenylmethoxy)carbonyl]-L-leucine, 2-(trimethylsilyl)ethyl ester (1.44 g., 2.42 mmole) [prepared in Example 2(a)] in dry methylene chloride (42 ml.) followed by the addition of pyridine-p-toluenesulfonic acid (0.12 g., 0.48 mmole). The reaction mixture is stirred at ambient temperature under nitrogen for 45 minutes, the diluted with ether (350 ml.), rinsed with water and brine, dried (MgSO$_4$), and concentrated in vacuo to give 2.0 g. of crude product. Flash chromatography on 113 g. of LPS-1 silica gel eluting with a gradient of from 100:1 to 25:1 petroleum ether:acetone yields 1.46 g. of (2S, 3S)-N-[[3-[(1,1-dimethylethoxy)carbonyl]-2,2-dimethyl-4-(2-methylpropyl)oxazolidin-5-yl]methyl]-N-[(phenylmethoxy)carbonyl]-L-leucine, 2-(trimethylsilyl)ethyl ester as an oil; $[\alpha]_D = -19.6°$ (c=1, chloroform). TLC (silica gel, 10:1 petroleum ether:acetone) $R_f = 0.53$.

(b) (2S, 3S)-N-[[3-[(1,1-Dimethylethoxy)carbonyl]-2,2-dimethyl-4-(2-methylpropyl)oxazolidin-5-yl]methyl]-N-[(phenylmethoxy)carbonyl]-L-leucinamide A solution of the 2-(trimethylsilyl)ethyl ester product from part (a) (1.5 g., 2.36 mmole) in dimethylformamide (12 ml.) is treated with tetra-n-butyl ammonium fluoride trihydrate (1.64 g., 5.2 mmole) and the reaction is stirred at ambient temperature for 4 hours. The reaction is diluted with 75 ml. of ether and ethyl acetate, then rinsed with 40 ml. of water (3 times) and brine, dried (MgSO$_4$), and concentrated in vacuo to give 1.16 g. of crude free acid.

This free acid (2.17 mmole) is dissolved in tetrahydrofuran (6.5 ml.), cooled to $-25°$ under argon, and then treated with N-methyl morpholine (219 mg., 2.17 mmole), followed by the slow careful addition of isobutylchloroformate (296 mg., 2.17 mmole). After five minutes, the reaction is treated carefully with 7N methanolic ammonia (1.3 ml., 9.11 mmole.), warmed to $-10°$ over a 30 minute period, then stoppered well, and stored in the refrigerator overnight. Afterward, the reaction is diluted with 70 ml. of ethyl acetate and ether, rinsed with water (3×20 ml.), 5% potassium bisulfate (30 ml.), water, and brine, dried (MgSO$_4$), and concentrated in vacuo to give 1.12 g. of crude product. The compound is purified by flash chromatography on 60 g. LPS-1 silica gel eluting with 2 column volumes of 2:1 chloroform:ethyl acetate followed by 20:1 chloroform:methanol. The product containing fractions are pooled to give 1.14 g. of (2S, 3S)-N-[[3-[(1,1-dimethylethoxy)carbonyl]-2,2-dimethyl-4-(2-methylpropyl)oxazolidin-5-yl]methyl]-N-[(phenylmethoxy)carbonyl]-L-leucinamide; $[\alpha]_D = -70.3°$ (c=1, methylene chloride). TLC (silica gel, 30:1 chloroform:methanol) $R_f = 0.40$.

Anal. calc'd. for $C_{29}H_{47}N_3O_6 \cdot 0.5H_2O$: C, 64.18; H, 8.92; N, 7.74. Found: C, 64.13; H, 8.59; N, 7.71.

(c) (2S, 3S)-[3-[[N-[(1,1-Dimethylethoxy)carbonyl]-L-phenylalanyl-3-[(phenylmethoxy)methyl]-L-histidyl]amino]-2-hydroxy-5-methylhexyl]-N$^2$-[(phenylmethoxy)carbonyl]-L-leucinamide A solution of the amide product from part (b) (445 mg., 0.83 mmole) in dry methylene chloride (5 ml.) is cooled in an ice-bath under nitrogen and treated with 5 ml. of distilled trifluoroacetic acid. The reaction is stoppered and stirred at room temperature. After one hour, the reaction is concentrated in vacuo, and the residue is dissolved in 4 ml. of distilled tetrahydrofuran, treated with 1N aqueous hydrochloric acid (1.8 ml., 1.8 mmole), stoppered, and stirred at ambient temperature. After 2 hours, the reaction is worked up by diluting with 10 ml. of saturated aqueous sodium bicarbonate, then extracted with chloroform (2×20 ml.). The organic extracts are combined, rinsed with brine, dried (MgSO$_4$), and concentrated in vacuo to 370 mg. of crude amino alcohol.

This amino alcohol (370 mg., 0.83 mmole) is dissolved in dry dimethylformamide (6.3 ml.) then treated with N-[N-[(1,1-dimethylethoxy)carbonyl]-L-phenylalanyl]-3-[(phenylmethoxy)methyl]-L-histidine (434 mg., 0.83 mmole) [prepared as set forth in Example 1(c)] and hydroxybenzotriazole trihydrate (127 mg., 0.83 mmole). The resulting solution is cooled in an ice-bath under nitrogen, then treated with dicyclohexylcarbodiimide (179 mg., 0.87 mmole), stoppered and refrigerated overnight. Afterwards, the reaction is diluted with 40 ml. of ethyl acetate and 10 ml. of ether, filtered to remove dicyclohexyl urea, and the filtrate is washed with 10 ml. portions of 5% aqueous potassium bisulfate, water, saturated aqueous sodium bicarbonate, water, and brine, dried (MgSO$_4$), and concentrated in vacuo to give 652 mg. of crude product. The compound is purified by flash chromatography on 60 g. of LPS-1 silica gel eluting with firstly 250 ml. of 2:1 chloroform:ethyl acetate, secondly with 100 ml. of a 1:1 mixture of 2:1 chloroform:ethyl acetate and 25:1 chloroform:methanol, and lastly with 25:1 chloroform:methanol. The product containing fractions are pooled to give 380 mg. of (2S,3S)-[3-[[N-[(1,1-dimethylethoxy)carbonyl]-L-phenylalanyl-3-[(phenylmethoxy)methyl]-L-histidyl]amino]-2-hydroxy-5-methylhexyl]-N$^2$-[(phneylmethoxy)carbonyl]-L-leucinamide; m.p. 90°-98°; $[\alpha]_D = -49.9°$ (c=1, chloroform). TLC (silica gel, 15:1 chloroform:methanol) $R_f = 0.25$.

Anal. calc'd. for $C_{49}H_{67}N_7O_9 \cdot 1H_2O$: C, 64.24; H, 7.59; N, 10.70. Found: C, 64.13; H, 7.46; N, 10.28.

(d) (2S,3S)-[3-[[N-[(1,1-Dimethylethoxy)carbonyl]-L-phenylalanyl-L-histidyl]amino]-2-hydroxy-5-methylhexyl]-L-leucinamide, diacetate salt A solution of the product from part (c) (350 mg., 0.39 mmole) in methanol (17.5 ml.) and water (3.5 ml.) is treated with 1N aqueous hydrochloric acid (0.86 ml., 0.86 mmole) and 20% palladium hydroxide on carbon catalyst (120 mg.). The reaction is treated with a balloon of hydrogen at room temperature overnight. Afterward, the catalyst is filtered off, and the filtrate is concentrated in vacuo to yield 350 mg. of crude product. The compound is purified by flash chromatography on 70 g. of LPS-1 silica gel eluting with 100:20:2.5:1 chloroform:methanol:water:acetic acid. The product containing fractions are pooled to yield 165 mg. of partially purified product and 74 mg. of fully purified product. The 165 mg. material is rechromatographed on 33 g. of LPS-1 silica gel eluting with the same solvent mixture. The product containing fractions are pooled and combined with the 74 mg. from the first column to give 210 mg. of (2S,3S)-[3-[[N-[(1,1-dimethylethoxy)-carbonyl]-L-phenylalanyl-L-histidyl]amino]-2-hydroxy-5-methylhexyl]-L-leucinamide, diacetate; m.p. 130°–131°; $[\alpha]_D = -20.4°$ (c=0.5, methanol). TLC (silica gel, 90:20:2.5:1 chloroform:methanol:water:acetic acid) $R_f = 0.19$.

Anal. calc'd. for $C_{33}H_{53}N_7O_6 \cdot 2C_2H_4O_2 \cdot 2H_2O$: C, 55.55; H, 8.19; N, 12.26. Found: C, 55.55; H, 7.83; N, 12.64.

EXAMPLES 6–23

Following the procedures of Examples 1 to 5, the aminoalcohol shown below in Col. I is reacted with the carboxylic acid shown in Col. II to give the product shown in Col. III.

| | Col. I | | | Col. II | | Col. III | |
|---|---|---|---|---|---|---|---|
| Example | $R_1$ | $R_2\text{—CH—CH—CH}_2\text{—N—CH—C—R}_4$ with $R_2$, OH, $R_1$, $R_3$, O above; $H_2N$ at left | | $R_6\text{—C(=O)—OH}$ | | $R_6\text{—C(=O)—NH—CH(R_2)—CH(OH)—CH}_2\text{—N(R_1)—CH(R_3)—C(=O)—R_4}$ | |
| | | $R_2$ | $R_3$ | | $R_4$ | $R_6$ | |
| 6 | —SO₂—C₆H₅ | —CH₂CH(CH₃)₂ | —CH₂CH(CH₃)₂ | | —NH₂ | (H₃C)₃C—O—C(=O)—NH—CH(CH₂-indol-3-yl)—C(=O)— | |
| 7 | —SO₂—C₆H₄—CH₃ | —CH₂CH(CH₃)₂ | —CH₂CH(CH₃)₂ | | —NH₂ | (H₃C)₃C—O—C(=O)—NH—CH(CH₂C₆H₅)—C(=O)— | |
| 8 | —CH₂—C₆H₅ | —CH₂CH(CH₃)₂ | —CH(CH₃)₂ | | —NH₂ | (H₃C)₃C—O—C(=O)—NH—CH(CH₃)—C(=O)—NH—CH(CH₂C₆H₅)—C(=O)— | |
| 9 | —CH₂—C₆H₅ | —CH₃ | —CH₃ | | —NH₂ | —CH₂—C₆H₅ | |
| 10 | —CH₂—C₆H₅ | —CH₂—C₆H₅ | —CH(CH₃)₂ | | —NH₂ | —CH₂-(thien-2-yl) | |
| 11 | —CH₂—C₆H₅ | —(CH₂)₂—C₆H₅ | —CH₂CH(CH₃)₂ | | —NH₂ | H₅C₂— | |
| 12 | —CH₂—C₆H₅ | —H | —CH₂—C₆H₅ | | —NH₂ | C₆H₅—CH₂—O—C(=O)—NH—CH(CH₂CH(CH₃)₂)—C(=O)— | |
| 13 | —CH₂—C₆H₅ | —CH₂-(indol-3-yl) | —H | | —NH₂ | C₆H₅—CH₂—C(=O)—NH—CH(CH₃)—C(=O)— | |
| 14 | —CH₂—C₆H₅ | —CH₂CCl₃ | —(CH₂)₂—C₆H₅ | | —NH₂ | (thien-2-yl)—CH₂—C(=O)—NH—CH₂—C(=O)— | |

-continued

| Example | Col. I $$H_2N-\underset{R_1}{CH}-\underset{OH}{CH}-CH_2-\underset{R_3}{N}-\underset{R_3}{CH}-\underset{}{\overset{O}{C}}-R_4$$ | | Col. II $$R_6-\overset{O}{C}-OH$$ | | Col. III $$R_6-\overset{O}{C}-NH-\underset{R_2}{CH}-\underset{OH}{CH}-CH_2-\underset{R_3}{N}-\underset{R_3}{CH}-\underset{}{\overset{O}{C}}-R_4$$ |
|---|---|---|---|---|---|
| | R$_1$ | R$_2$ | R$_3$ | R$_4$ | R$_6$ |
| 15 | —CH$_2$—C$_6$H$_5$ | —CH$_2$—C$_6$H$_{11}$ | —C$_2$H$_5$ | —NH$_2$ | pyrrole-C(O)—NH—CH(CH$_2$C$_6$H$_5$)— |
| 16 | —CH$_2$—C$_6$H$_5$ | —(CH$_2$)$_4$—NH—CH$_2$—C$_6$H$_5$ | —CH(CH$_3$)$_2$ | —NH$_2$ | H$_3$C—C(O)—NH—CH(CH$_2$—N=CH—C$_6$H$_5$)— |
| 17 | —CH$_2$—C$_6$H$_5$ | —CH$_2$CH(CH$_3$)$_2$ | —CH$_2$CH(CH$_3$)$_2$ | —NH—CH$_2$—C$_6$H$_5$ | C$_6$H$_5$—O—CH$_2$—C(O)—NH—CH(CH$_2$C$_6$H$_5$)— |
| 18 | —CH$_2$—C$_6$H$_5$ | —CH$_2$CH(CH$_3$)$_2$ | —CH$_2$—NH—C(=NH)—NH$_2$—NO$_2$ | —NH—CH$_3$ | C$_6$H$_5$—CH$_2$—O—C(O)—NH—CH$_2$—C(O)—NH—CH(CH$_2$CH(CH$_3$)$_2$)— |
| 19 | —CH$_2$—C$_6$H$_5$ | —CH$_2$—S—CH$_3$ | —CH$_2$CH(CH$_3$)$_2$ | —OCH$_3$ | C$_6$H$_5$—CH$_2$—O—C(O)—NH—CH(CH$_2$-naphthyl)—C(O)—NH—CH(CH$_2$C$_6$H$_5$)— |
| 20 | —CH$_2$—C$_6$H$_5$ | —CH$_2$CH(CH$_3$)$_2$ | —CH$_2$CH(CH$_3$)$_2$ | —O—CH$_2$—C$_6$H$_5$ | (H$_3$C)$_3$C—O—C(O)—NH—CH(CH$_2$C$_6$H$_5$)—C(O)—NH—CH(CH$_2$—N=CH—O—CH$_2$—C$_6$H$_5$)— |

-continued
| Example | Col. I | | | Col. II | | Col. III |
|---|---|---|---|---|---|---|
| | $H_2N-CH(R_2)-CH(OH)-CH_2-N(R_1)-CH(R_3)-C(=O)-R_4$ | | | $R_6-C(=O)-OH$ | | $R_6-C(=O)-NH-CH(R_2)-CH(OH)-CH_2-N(R_1)-CH(R_3)-C(=O)-R_4$ |
| | $R_1$ | $R_2$ | $R_3$ | $R_6$ | $R_4$ | $R_6$ |
| 21 | —CH$_2$—C$_6$H$_5$ | —CH$_2$CH(CH$_3$)$_2$ | —CH$_2$CH(CH$_3$)$_2$ | —CH$_2$CH(CH$_3$)$_2$ | —NH$_2$ |  |
| 22 | —CH$_3$ | —CH$_2$—S—CH$_2$—C$_6$H$_5$ | —CH$_3$ | | —NH$_2$ |  |
| 23 | —CH$_2$—C$_6$H$_5$ | —CH$_2$CH(CH$_3$)$_2$ | —CH$_2$CH(CH$_3$)$_2$ | | —NH$_2$ |  |

The R1 protecting group shown in Examples 8 to 21 and 23, the R2 protecting groups shown in Examples 16 and 22, the R3 protecting group shown in Example 18 are removed as the last step in the synthesis as can the R11 group shown in Examples 16, 20 and 22 and the R6 protecting group shown in Examples 12, 18, and 19.

In a similar manner, by employing the corresponding aminoketone of the formula

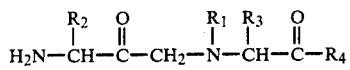

within the procedure of Examples 6 to 23 other compounds within the scope of the invention are obtained.

EXAMPLE 24

1000 tablets each containing the following ingredients

| | |
|---|---|
| $N^2$—[3-[[N—[N—[(1,1-Dimethylthoxy)carbonyl]-L-phenylalanyl]-L-histidyl]amino]-2-hydroxy-5-methylhexyl]-N—[2-(2-pyridyl)ethyl]-L-leucinamide, acetic acid salt (1:2) | 250 mg. |
| Cornstarch | 100 mg. |
| Gelatin | 20 mg. |
| Avicel (microcrystalline cellulose) | 50 mg. |
| Magnesium stearate | 5 mg. |
| | 425 mg. | are prepared from sufficient bulk quantities by mixing $N^2$-[3-[[N-[N-[(1,1-dimethylethoxy)carbonyl]-L-phenylalanyl]-L-histidyl]amino]-2-hydroxy-5-methylhexyl]-N-[2-(2-pyridyl)ethyl]-L-leucinamide, acetic acid salt (1:2) and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 250 mg. of active ingredient.

In a similar manner, tablets containing 250 mg. of the product of any of Examples 2 to 23 can be prepared.

A similar procedure can be employed to form tablets containing 500 mg. of active ingredient.

EXAMPLE 25

Two piece #1 gelatin capsules are filled with a mixture of the following ingredients:

| | |
|---|---|
| (2R,3S)-[3- [[N—[(1,1-Dimethylethoxy)carbonyl-L-phenylalanyl-L-histidyl]]amino]-2-hydroxy-5-methylhexyl]-L-leucinamide, diacetate salt | 500 mg. |
| Magnesium stearate | 7 mg. |
| Lactose | 193 mg. |
| | 700 mg. |

In a similar manner capsules containing 500 mg. of the product of any of Examples 1 and 3 to 23 can be prepared.

EXAMPLE 26

An injectable solution is prepared as follows:

| | |
|---|---|
| N—[(3S)-3-[[N—[(1,1-Dimethylethoxy)carbonyl]-3-[(phenylmethoxy)methyl]-L-histidyl]amino]-2-hydroxy-5-methylhexyl]-L-leucinamide, diacetate salt | 1000 g. |
| Methyl paraben | 5 g. |
| Propyl paraben | 1 g. |
| Sodium chloride | 5 g. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 200 mg. of active ingredient per ml. of solution for injection.

In a similar manner, an injectable solution containing 200 mg. of active ingredient per ml. of solution can be prepared for the product of any of Examples 1, 2 and 4 to 23.

EXAMPLE 27

1000 tablets each containing the following ingredients:

| | |
|---|---|
| (2S,3S)-[3-[[N—[(1,1-Dimethylethoxy)carbonyl]-L-phenylalanyl-L-histidyl]amino]-2-hydroxy-5-methylhexyl]-L-leucinamide, diacetate salt | 500 mg. |
| Avicel | 300 mg. |
| Hydrochlorothiazide | 14.5 mg. |
| Lactose | 113 mg. |
| Cornstarch | 15.5 mg. |
| Stearic Acid | 7 mg. |
| | 950 mg. | are prepared from sufficient bulk quantities of slugging the (2S,3S)-[3-[[N-( 1,1-dimethylethoxy)carbonyl]-L-phenylalanyl-L-histidyl]amino]-2-hydroxy-5-methylhexyl]-L-leucinamide, diacetate salt, Avicel, and a portion of the stearic acid. The slugs are ground and passed through a #2 screen, then mixed with the hydrochlorothiazide, lactose, cornstarch, and remainder of the stearic acid. The mixture is compressed into 950 mg. capsule shaped tablets in a tablet press.

In a similar manner, tablets can be prepared containing 500 mg. of the product of any of Examples 1 to 4 and 6 to 23.

What is claimed is:

1. A compound of the formula

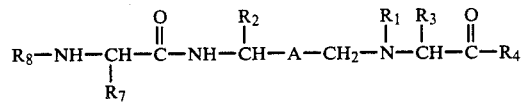

including a pharmaceutically acceptable salt thereof wherein:

A is

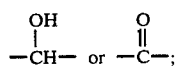

R4 is —O—lower alkyl, —O—(CH2)m—aryl, or —O—(CH2)m—heterocyclo;

m is zero, one, two, three or four;

R8 is hydrogen,

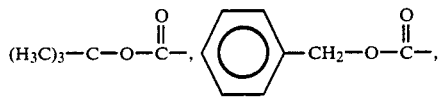

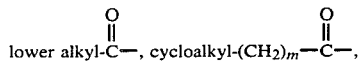

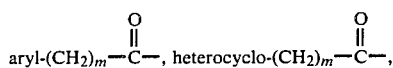

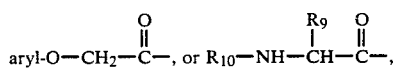

R$_{10}$ is hydrogen,

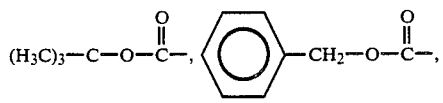

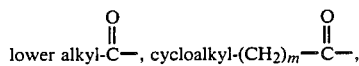

, or

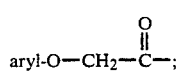

R$_2$, R$_3$, R$_7$ and R$_9$ are independently selected from the group consisting of hydrogen, lower alkyl, halo substituted lower alkyl, —(CH$_2$)$_n$—aryl, —(CH$_2$)$_n$—heterocyclo, —(CH$_2$)$_n$—OH, —(CH$_2$)$_n$—NH$_2$, —(CH$_2$)$_n$—SH, —(CH$_2$)$_n$—S—lower alkyl, —(CH$_2$)$_2$—S—(CH$_2$)$_2$—NH$_2$,

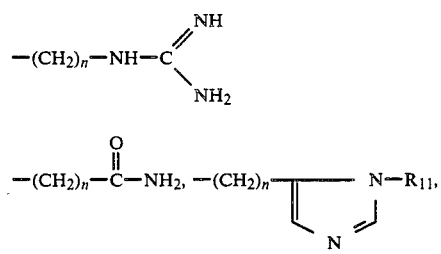

and —(CH$_2$)$_n$—cycloalkyl;
n is an integer from 1 to 4;
R$_{11}$ is

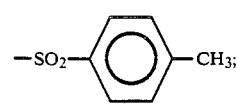

R$_1$ is hydrogen, lower alkyl, —(CH$_2$)$_n$—aryl, —(CH$_2$)$_n$—cycloalkyl,

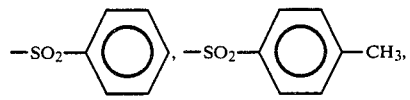

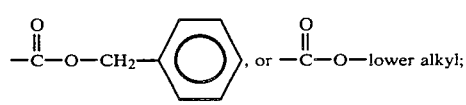

the term lower alkyl refers to straight or branched chain radicals having up to seven carbon atoms;

the term cycloalkyl refers to saturated rings of 4 to 7 carbon atoms;

the term halogen refers to Cl, Br, and F;

the term halo substituted lower alkyl refers to such lower alkyl groups in which one or more hydrogens have been replaced by Cl, Br, or F groups;

the term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH—alkyl wherein alkyl is of 1 to 4 carbons, or —N(alkyl)$_2$ wherein alkyl is of 1 to 4 carbons, di or tri substituted phenyl, 1-naphthyl or 2-naphthyl wherein said substituents are methyl, methoxy, methylthio, halogen, or hydroxy; and the term heterocyclo refers to 2-thienyl, 3-thienyl, 2-furyl, 3-furyl, 2-pyridyl, 3-pyridyl, 4-pyridyl, imidazolyl, and indolyl.

2. A compound of claim 1 wherein:
A is

3. A compound of claim 1 wherein:
A is

4. A compound of claim 3 wherein:
R$_1$ is hydrogen,

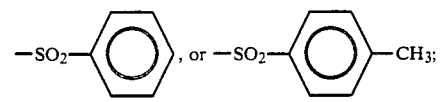

R$_2$ is straight or branched chain lower alkyl of 1 to 4 carbons, benzyl, phenethyl or

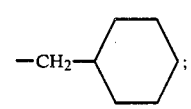

R$_3$ is hydrogen, straight or branched chain lower alkyl of 1 to 4 carbons, benzyl or phenethyl;
R$_7$ is

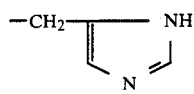
or
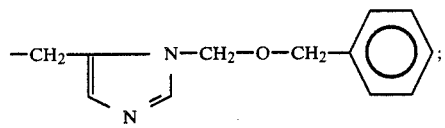
R₈ is
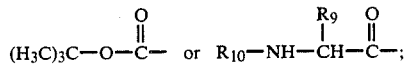
R₉ is —(CH₂)ₙ—aryl wherein aryl is phenyl or 1-naphthyl and n is one or two; and
R₁₀ is
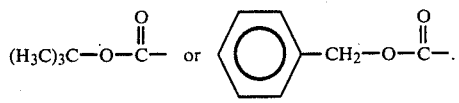
5. A compound of claim 4 wherein
R₁ is hydrogen;
R₂ is —CH₂—CH(CH₃)₂;
R₃ is —CH₂—CH(CH₃)₂ or —CH(CH₃)₂;
R₇ is
R₉ is
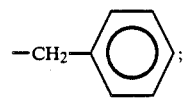
and
R₁₀ is
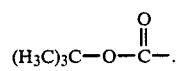
* * * * *